United States Patent
Roof et al.

(10) Patent No.: US 9,901,661 B2
(45) Date of Patent: Feb. 27, 2018

(54) PEELABLE HEAT-SHRINK TUBING

(71) Applicant: Zeus Industrial Products, Inc., Orangeburg, SC (US)

(72) Inventors: Irina Puzdrjakova Roof, Lexington, SC (US); Brian Robert Tomblin, Columbia, SC (US); Zeth Eberling, Lexington, SC (US); Bruce L. Anneaux, Lexington, SC (US); Douglas Lee Tourville, Orangeburg, SC (US)

(73) Assignee: Zeus Industrial Products, Inc., Orangeburg, NC (US)

( * ) Notice: Subject to any disclaimer, the term of this patent is extended or adjusted under 35 U.S.C. 154(b) by 0 days.

(21) Appl. No.: 15/242,677

(22) Filed: Aug. 22, 2016

(65) Prior Publication Data

US 2017/0095597 A1 Apr. 6, 2017

Related U.S. Application Data

(63) Continuation of application No. 14/753,115, filed on Jun. 29, 2015, now Pat. No. 9,440,044, which is a continuation of application No. 14/732,372, filed on Jun. 5, 2015, now abandoned.

(60) Provisional application No. 62/008,708, filed on Jun. 6, 2014.

(51) Int. Cl.
*A61L 29/04* (2006.01)
*A61M 25/00* (2006.01)

(52) U.S. Cl.
CPC ........... *A61L 29/041* (2013.01); *A61L 29/049* (2013.01); *A61M 25/0009* (2013.01); *A61M 25/0045* (2013.01)

(58) Field of Classification Search
CPC ................ A61L 29/041; A61L 29/049; A61M 25/0045; A61M 25/0009
See application file for complete search history.

(56) References Cited

U.S. PATENT DOCUMENTS

| 4,029,868 A | 6/1977 | Carlson |
| 4,568,275 A | 2/1986 | Sakurai |
| 5,015,512 A | 5/1991 | Matsumoto |

(Continued)

FOREIGN PATENT DOCUMENTS

| EP | 1 605 014 | 12/2005 |
| EP | 2 338 935 A1 | 6/2011 |

(Continued)

OTHER PUBLICATIONS

Notification of Reasons for Refusal dated Jun. 6, 2016, for co-pending Japanese patent application No. 2017-516643.

(Continued)

*Primary Examiner* — Michael C Miggins
(74) *Attorney, Agent, or Firm* — Louis Isaf; Womble Bond Dickinson (US) LLP

(57) ABSTRACT

A heat shrink tubing, which can be readily peeled in the longitudinal direction after use (e.g., to remove the heat shrink tubing from an underlying material) is provided herein. The heat shrink tubing can be of various compositions, and generally is produced from at least one fluorinated, copolymeric resin. The tubing can exhibit desirable physical properties such as good optical clarity (e.g., translucency or transparency) and/or peelability, exhibiting one or more of complete, straight, and even peeling along a given length of tubing.

20 Claims, 2 Drawing Sheets

(56) References Cited

U.S. PATENT DOCUMENTS

| | | | |
|---|---|---|---|
| 5,317,061 A | 5/1994 | Chu et al. | |
| 5,549,552 A | 8/1996 | Peters et al. | |
| 5,599,631 A | 2/1997 | Chen et al. | |
| 5,858,540 A | 1/1999 | Hayami et al. | |
| 6,402,677 B1 | 6/2002 | Jacobs | |
| 8,252,219 B2 | 8/2012 | Trapp | |
| 2002/0157350 A1 | 10/2002 | Dickey et al. | |
| 2005/0182387 A1 | 8/2005 | Webler | |
| 2005/0278018 A1 | 12/2005 | Jensen | |
| 2007/0020413 A1 | 1/2007 | Moriuchi et al. | |
| 2008/0048011 A1 | 2/2008 | Weller | |
| 2010/0221522 A1 | 9/2010 | Mrozinski | |
| 2011/0083878 A1 | 4/2011 | Brown et al. | |
| 2011/0192632 A1 | 8/2011 | Abe et al. | |
| 2011/0264057 A1 | 10/2011 | Eversull et al. | |
| 2012/0010369 A1 | 1/2012 | Iizuka et al. | |
| 2014/0255633 A1 | 9/2014 | Suzuki et al. | |
| 2015/0080506 A1 | 3/2015 | Kurosaki | |

FOREIGN PATENT DOCUMENTS

| | | |
|---|---|---|
| JP | S63-283929 | 11/1988 |
| JP | H 03-212441 | 9/1991 |
| JP | 7-235743 | 9/1995 |
| JP | H08-12767 | 1/1996 |
| JP | 8-216252 | 8/1996 |
| JP | H09-31285 | 2/1997 |
| JP | 2001-190681 | 7/2001 |
| JP | 2002-12731 | 1/2002 |
| JP | 2007-179889 | 7/2007 |
| JP | 2007-321817 | 12/2007 |
| JP | 2008-20037 | 1/2008 |
| JP | 2011-032359 A | 2/2011 |
| WO | WO 94/05712 | 3/1994 |
| WO | WO 99/64097 | 12/1999 |
| WO | WO 2008/007680 | 1/2008 |
| WO | WO 2008-109863 A2 | 9/2008 |
| WO | WO 2009/094089 | 7/2009 |
| WO | WO 2010/005755 | 1/2010 |
| WO | WO 2010/048186 | 4/2010 |
| WO | WO 2013/074452 | 5/2013 |

OTHER PUBLICATIONS

Notification of Transmittal of The International Search Report & The Written Opinion of the International Searching Authority, or the Declaration from co-pending International Applicaiton No. PCT/US2015/034536.
Daikin Industries Fluoroplastics—EC-61k—Product Information—Daikin Industries. Ltd.—pp. 1-24—Oct. 2001.
On-Sale: Junflon Peelable Heat Shrink Tube, sold by Junkosha, Inc., Jul. 2014.
Re-Submission of Third-Party Submission Under 35 U.S.C. 122(e) and 37 C.F.R. §1.290 filed in co-pending U.S. Appl. No. 14/732,372, filed Jun. 5, 2015.
PCT Third Party Observation (PCT Administrative Instructions Part 8) dated Oct. 6, 2016, filed in International Application No. PCT/US2015/034536.

PEELABLE HEAT-SHRINK TUBING

CROSS-REFERENCE TO RELATED APPLICATION

The present application is a continuation application of U.S. application Ser. No. 14/753,115, filed Jun. 29, 2015; which application is a continuation application of U.S. application Ser. No. 14/732,372, filed Jun. 5, 2015; which application claims priority to U.S. Provisional Patent Application No. 62/008,708, filed Jun. 6, 2014; all of which are incorporated herein by this reference.

FIELD OF THE INVENTION

The present application is directed to heat shrink polymeric tubing and methods for making such heat shrink polymeric tubing, which finds application in a variety of fields.

BACKGROUND OF THE INVENTION

Heat shrink tubing generally comprises a plastic material that is extruded into a tubular form and expanded. The extruded and expanded tube is designed to shrink (i.e., decrease in diameter) when heated to a given temperature. As such, heat shrink tubing can serve various functions. It can provide a tight, protective jacketing to closely cover and insulate various elements (e.g., to protect them from abrasion and to provide thermal, chemical, moisture, and/or electrical insulation); it can serve to bundle certain elements together (i.e., within the same heat shrink tube); it can serve to seal/isolate certain elements from others; it can be used to join/fuse two elements, e.g., two tubes together; and it can serve to modify the properties of an underlying material (e.g., by closing around another material and shrinking that material as well). These capabilities render the tubing useful for various purposes and heat shrink tubing finds use across various fields, e.g., medical, chemical, electrical, optical, electronic, aerospace, automotive, and telecommunications fields.

In the medical context, heat shrink tubing is particularly beneficial in designing increasingly small and more complex devices to be inserted into the body (e.g., catheters, endoscopes, etc.). One representative medical use of heat shrink tubing is in the context of manufacturing a guide catheter, comprising a tubular structure having an inner layer of a polymer, a middle layer of a wire braid and an outer layer of another polymer. To assemble such catheters, an expanded heat shrink tube is typically applied to an assembled shaft around a mandrel and the assembly is exposed to high temperature sufficient to shrink the heat shrink tube. Under these conditions, the outer polymeric layers within the catheter shaft melt and flow, and the heat shrink tube contracts, providing compressive forces such that the inner and outer polymeric layers of the catheter shaft can bond together, encapsulating the wire braid within. The heat shrink tubing is then removed and discarded and the catheter assembly is removed from the mandrel. See, e.g., the disclosures of U.S. Pat. No. 7,306,585 to Ross and U.S. Pat. No. 5,755,704 to Lunn, which are incorporated herein by reference.

Thus, although heat shrink tubing is an essential feature of some final products, in many applications (particularly in medical applications), the heat shrink tubing is involved only in the manufacturing of the final product and is removed from the final product prior to use. Therefore, an additional step involved in the use of heat shrink tubing in certain applications, is removal of the heat shrink tubing from the underlying material. Removability of heat shrunk tubing following use thereof can be facilitated by a score line or indentations/perforations added prior or subsequent to use (i.e., heating) of the heat shrink tubing. After use, the heat shrink tubing can be torn along the scored line or indentations/perforations and discarded. Alternatively, a non-pre-scored heat shrink tube is scored down the length of the tubing following use (i.e., after being shrunk), and the tubing is then torn along the line and discarded.

The nick or score line to facilitate tearing must be at the proper depth to facilitate tearing without damaging the underlying material. If the nick or score line is too deep or if the tubing does not tear perfectly along the score line or indentations/perforations, the medical device can be rendered useless. Accordingly, there is a need for a tubing that can be applied to device components to encapsulate and compress them as needed, wherein the tubing can be readily and reliably removed (even with a non-uniform geometry, which may be difficult to score to a precise depth) with minimal potential to damage the underlying device components.

SUMMARY OF THE INVENTION

The present invention relates to heat shrink tubing of various compositions. In certain embodiments, the heat shrink tubing described herein is described as "peelable," and can be readily peeled or torn apart in the longitudinal direction (e.g., to remove the heat shrink tubing from an underlying material). This peelability can advantageously allow for the tubing to be provided, used, and removed, in some embodiments, in the absence of any scoring, break lines, indentations, or perforations along the length of the tubing. In certain embodiments, a small score at the end of a length of tubing can allow one to peel the tubing for a significant length, including the full length of the tubing, providing two substantially equal halves of tubing following complete peeling of the length of tubing. The disclosed tubing can, in some embodiments, exhibit one or more of complete, straight, and even peeling along a given length of the tubing.

In one aspect, the present disclosure provides a tubing, comprising at least one thermoplastic, melt processable fluoropolymer resin, wherein the tubing is less than about 40% crystalline as determined by x-ray diffraction; and wherein the tubing exhibits heat shrink capability, longitudinal peelability, and translucency or transparency through a wall of the tubing. In another aspect is provided. In certain embodiments, such tubings exhibit a melting point onset of less than about 230° C.

In another aspect, the present disclosure provides a tubing, comprising at least one thermoplastic, melt processable fluoropolymer resin, wherein the tubing exhibits a melting point onset of less than about 230° C.; and wherein the tubing exhibits heat shrink capability, longitudinal peelability, and translucency or transparency through a wall of the tubing.

In certain embodiments, such tubings can comprise no more than one resin and in other embodiments, such tubings can comprise two or more resins (e.g., a main resin and one or more secondary resins). The resin or resins in these tubings can vary and can, in some embodiments, comprise a fluorinated ethylene propylene resin. In some embodiments, the at least one resin comprises one or more resins selected from the group consisting of polyvinylidene fluoride, perfluoroalkoxy alkane (PFA), perfluoro(alkyl vinyl ethers) (PAVE), a tetrafluoroethylene, hexafluoropropylene, and vinylidine fluoride terpolymer (THV), poly(ethylene-co-tetrafluoroethylene) (ETFE), ethylene chlorotrifluoroethylene (ECTFE), polychlorotrifluoroethylene (PCTFE), polytetrafluoroethylene (PTFE), tetrafluoroethylene and perfluoromethylvinyl ether copolymer (MFA), and copolymers, blends, and derivatives thereof. For example, in one particular embodiment, the tubing may comprise an FEP resin as the main resin (e.g., in an amount of at least about 50% by weight) and one or more secondary resins selected from the list above.

In a further aspect of the disclosure is provided a tubing, comprising no more than one thermoplastic, melt processable fluoropolymer resin, wherein the tubing exhibits heat shrink capability, longitudinal peelability, and translucency or transparency through a wall of the tubing. In some embodiments, such a tubing can consist essentially of a single thermoplastic melt processable fluoropolymeric resin (e.g., a binary fluorinated copolymer). Exemplary resins for such tubings include, but are not limited to, fluorinated ethylene propylene (FEP), polyvinylidene fluoride, perfluoroalkoxy alkane (PFA), perfluoro(alkyl vinyl ethers) (PAVE), a tetrafluoroethylene, hexafluoropropylene, and vinylidine fluoride terpolymer (THV), poly(ethylene-co-tetrafluoroethylene) (ETFE), ethylene chlorotrifluoroethylene (ECTFE), polychlorotrifluoroethylene (PCTFE), polytetrafluoroethylene (PTFE), tetrafluoroethylene and perfluoromethylvinyl ether copolymer (MFA), and copolymers and derivatives thereof. In some embodiments, such tubings can exhibit a melting point onset of less than about 230° C. In some embodiments, such tubings can be less than about 40% crystalline as determined by x-ray diffraction.

With regard to the described herein, in some embodiments, the tubings comprise no physical score line, cut, or nick. In certain embodiments, the longitudinal peelability does not require a physical score line, cut, or nick or wherein the longitudinal peelability requires a physical score line, cut, or nick that is less than about $1/50^{th}$ the length of the tubing. The tubings described herein can, in some embodiments, exhibit translucency or transparency such that the total light transmittance through the wall of tubing is about 90% or greater and wherein the diffuse light transmittance through the wall of the tubing is about 25% or less.

In a further aspect of the present disclosure is provided a method of using the tubings described herein. In one embodiment is provided a method of using a tubing as disclosed herein, comprising: applying the tubing around at least a portion of a device comprising multiple components; heating the tubing to cause the tubing to shrink in diameter; cooling the shrunk tubing; and peeling the shrunk tubing from the device to allow for a consistent longitudinal tearing (e.g., in some embodiments, giving two tubing halves of substantially equal size). In a particular embodiment, the method can further comprise nicking or cutting the tubing across the cross-sectional diameter at an end of the tubing, wherein the length of the resulting nick or cut is short with respect to the length of tubing (e.g., less than about $1/50^{th}$ the length of the tubing) to facilitate the peeling.

In a still further aspect of the present disclosure is provided a method of preparing certain tubings disclosed herein, comprising: selecting a resin or resins that exhibit a melting point onset of less than about 230° C., a percent crystallinity of less than about 40% by x-ray diffraction or both a melting point onset of less than about 230° C., a percent crystallinity of less than about 40% by x-ray diffraction; and extruding the resin or resins into a tubing exhibiting heat shrink capability, longitudinal peelability, and translucency or transparency through a wall of the tubing.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION

Figure 1:
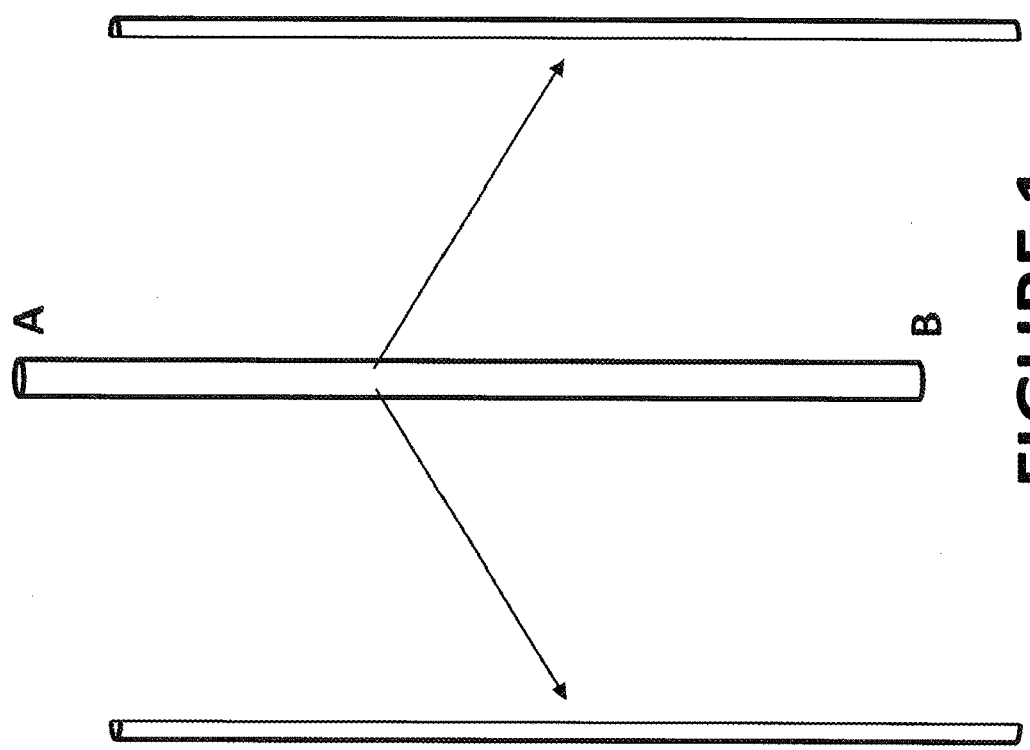
FIG. 1 is a schematic representation of the "peelable" nature of certain tubings disclosed in the present application.

The present invention will now be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements Like numbers refer to like elements throughout.

The disclosure relates to tubing comprising a material prepared from one or more polymeric resins. In certain embodiments, the tubings provided herein exhibit desirable combinations of physical properties. For example, in some embodiment, the tubings can be described as "peelable," or "tearable" in the longitudinal direction, which will be described further herein. In some embodiments, the tubings can be described as exhibiting translucency or transparency (e.g., optical clarity). In some embodiments, the tubings can be described as exhibiting heat shrink capabilities. Advantageously, the present disclosure provides polymeric tubings that exhibit a combination of heat shrink capability, longitudinal peelability, and/or translucency (e.g., two or all three of these properties).

"Resin" as used herein refers to a material consisting essentially of a given type of polymer (e.g., a copolymer). Resins are typically provided in solid form (e.g., as solid pellets), although they are not limited thereto (with other forms including, but not limited to, powders, granules, dispersions, solutions, gels, and the like). In certain embodiments, polymeric resins are homopolymeric (i.e., comprising a single type of repeating monomer unit). In certain embodiments, polymeric resins are copolymeric resins, comprising, for example, alternating copolymers (having two or more monomer units in a regularly alternating arrangement), periodic copolymers (having two or more monomer units in a regularly repeating sequence), block copolymers (having two or more individual types of monomer segments connected by a covalent bond), or random copolymers (having two or more monomer units randomly arranged with respect to one another). In certain embodiments, polymeric resins can comprise binary copolymers (i.e., comprising two types of repeating monomer units). In certain embodiments, polymeric resins are terpolymeric (i.e., comprising three types of repeating monomer units). The compositions and molecular weights of the polymers in a particular resin can vary, as generally understood and as further described below.

In various embodiments, the tubings disclosed herein comprise one or more fluorinated polymeric resins (e.g., as the sole resin component of a single-resin tubing or as the main polymeric resin and/or some or all secondary resin(s) of a multi-resin tubing). Any fluorinated polymeric resin can be used according to the present disclosure. Of particular relevance to the present disclosure are thermoplastic, melt-processable fluoropolymeric resins. Certain such resins are disclosed, for example, in U.S. Patent Application Publication No. 2014/0255633 to Suzuki et al., which is incorporated herein by reference. Particular resins and combinations of resins can lead to unexpected results, as will be detailed herein.

Exemplary fluorinated resins that are useful according to the present disclosure include, but are not limited to, resins comprising, consisting of, or consisting essentially of, fluorinated ethylene propylene (FEP), polyvinylidene fluoride (PVDF), perfluoroalkoxy alkanes (PFA), perfluoro (alkyl vinyl ethers) (PAVE) (e.g., perfluoro (methyl vinyl) ether, PMVE or perfluoro (propyl vinyl) ether (PPVE)), a terpolymer of tetrafluoroethylene, hexafluoropropylene and vinylidene fluoride (THV), poly(ethylene-co-tetrafluoroethylene) (ETFE), ethylene chlorotrifluoroethylene (ECTFE), polychlorotrifluoroethylene (PCTFE), polytetrafluoroethylene (PTFE), a copolymer of tetrafluoroethylene and perfluoromethylvinyl ether (MFA); and copolymers, blends, and derivatives thereof. In certain embodiments, the resin component of a single-resin tubing or the main polymeric resin of a multi-resin tubing is FEP. As such, in certain embodiments, the tubings disclosed herein can consist of an FEP resin, can consist essentially of an FEP resin or can comprise an FEP resin.

In some embodiments, the tubings provided are prepared from a single resin ("single-resin tubing"), which can be selected from the exemplary resins disclosed herein. Such tubings will be described as being prepared from and comprising no more than one resin (i.e., a single resin). In specific embodiments, certain single resin tubings can be prepared from and consist essentially of (or consist of) one resin.

Certain tubing provided herein is prepared from two or more polymeric resins ("multi-resin tubing") and will be described as being prepared from and comprising a "main polymeric resin" and one or more "secondary polymeric resins." The ratio of the main polymeric resin to the secondary polymeric resin(s) in such tubings can range, e.g., from about 60:40 to about 98:2. In certain embodiments, the ratio of the main polymeric resin to the secondary polymeric resin(s) can be between about 70:30 to about 95:5, between about 80:20 and about 90:10. Multi-resin tubings can, in some embodiments, be described as being prepared from such main and secondary polymeric resins, wherein the main polymeric resin is in an amount of at least about 60% by weight, at least about 70% by weight, at least about 75% by weight, at least about 80% by weight, at least about 85% by weight, at least about 88% by weight, or at least about 90% by weight. Multi-resin tubings can alternatively be described as being prepared from such main and secondary polymeric resins, wherein the secondary polymeric resin (or resins) is provided in an amount up to about 30% by weight, up to about 20% by weight, up to about 15% by weight, up to about 12% by weight, up to about 10% by weight, or up to about 8% by weight. It is noted that preferable polymeric resin ratios in multi-resin tubings may, in some embodiments, be dependent on the tubing diameter and expansion ratio of a given tubing. In other words, to prepare tubing having different diameters and/or different expansion ratios, different polymeric resin ratios may advantageously be employed.

In a multi-resin tubing, the one or more secondary resins may be fluorinated or non-fluorinated. With regard to fluorinated resins, the secondary resin may, in some embodiments, comprise a resin selected from the list above (wherein the secondary resin(s) are different than the main polymeric resin). The main and secondary polymeric resin(s) typically differ from one another in chemical composition but may, in certain embodiments, differ from one another only in, e.g., polymer molecular weight. In other embodiments, the secondary polymeric resin may be a non-fluorinated resin. Exemplary non-fluorinated resins that may be useful in the tubing provided herein include, but are not limited to, polyether ether ketone (PEEK), and polyethylene (PE) (including low density polyethylene, LDPE).

In one particular embodiment, the secondary resin of a multi-resin tubing can comprise a liquid crystal polymer (LCP). The particular LCP employed can vary. It is noted that, although not limited, in some embodiments employing LCP, the resulting tubing may not exhibit heat shrink properties.

In another particular embodiment, the secondary resin can comprise a PTFE powder. The type of PTFE powder that is incorporated in such embodiments can vary and may include conventional PTFE extrusion grade powder as well as PTFE granules, particles, and the like of various particle sizes. The incorporation of PTFE powder within a given type of tubing may, in some embodiments, increase the peelability of that tubing. Exemplary combinations of main polymeric resins and secondary polymeric resins include, but are not limited to: FEP and PFA; FEP and PVDF; FEP and ETFE; FEP and LDPE; FEP and PEEK; FEP and THV; and FEP and LCP.

In multi-resin tubings, selection of the component resins can, in some embodiments, be made based on the desired end product, as will be described more fully herein. Although not intended to be limiting, for example, where an optically clear tubing is desired, resins with similar refractive indices are advantageously selected. Alternatively, resins with dissimilar refractive indices may be modified to bring the apparent refractive indices of the two or more resins closer to one another such that optical clarity and light transmittance are improved and the resulting tubing produced from the modified resin(s) is optically clear as well. Furthermore, a single resin that can be made into a heat shrink product with peelability but is otherwise not optically clear or has high haze, can be modified chemically or with additives to achieve all the objects of the present invention. Similarly, any material modification or manipulation that may enable a tubing meeting the improvements of the present invention to be realized are included. As another example, again not intended to be limiting, it may be advantageous in certain embodiments to select resins with somewhat different melting points (e.g., substantially different melting points), as generally described herein.

The present disclosure further provides methods of processing these and other resins to provide tubings. In general, the methods by which such single-component resin and multi-component resin peelable, heat-shrink tubings are prepared can vary. Generally, the desired resin or resins are formed into a tubular form, e.g., via extrusion and then mechanically expanded. The means by which these steps can be conducted can vary, as will be described herein.

Where two or more resins are used to form a multi-resin tube, the main and secondary resin(s) are generally combined in some manner prior to the forming (e.g., extrusion)

process. In one particular embodiment, the main polymeric resin and secondary resin(s) are provided in a given ratio (e.g., each resin in independent pellet form), the two or more resins (e.g., the two types of pellets) are blended, and the blend is heated and directly extruded to provide tubing. This method is referred to herein as the "blending" method. In another embodiment, the main polymeric resin and secondary resin(s) are first formed into a compounded premix, also referred to as a "compounded pellet" or a "premix resin." In such embodiments, the main polymeric resin and secondary polymeric resin(s) are mixed and heated in independent pellet form such that a new material comprising the main and secondary polymeric resins is produced and formed into a compounded pellet, which may, in some embodiments, have a reasonably uniform distribution of main and secondary polymeric resins throughout. The compounded pellets are then extruded to provide tubing. Accordingly, this latter method adds an additional heat cycle (i.e., in the production of the compounded pellets) as compared with the "blending" method. This method is referred to herein as the "premix" method.

The single resin, the "blended" combination of resins, or the "premix resin" is formed into a tube, e.g., by subjecting the resin or resins to extrusion. Extrusion generally comprises placing the desired resin or resins (typically in pellet form) into an extruder (e.g., a screw extruder). Within the extruder, the resin or resins are heated, compressed, and forced through an annular die set, creating a tube. Tubes of various diameters and lengths can be produced. The tube dimensions can be set by the tooling size on the extrusion line and this and other parameters of the extrusion step can be adjusted and optimized to produce the desired tubing. In some embodiments, tubing having a relatively uniform wall thickness is provided. In some embodiments, tubing can be extruded with one or more embedded stripes in the wall such that regions of weakness are defined which can enhance the peelability of certain compositions disclosed herein.

The extruded tubular form is then typically radially expanded (e.g., by mechanical means) to provide an expanded tubing material that can function as a heat shrink material (i.e., a material which, when heated, returns to its unexpanded form, and consequently "shrinks"). The expansion can be either in-line with extrusion, or offline (i.e., conducted independently of the extrusion process). All means for radial expansion of tubing are intended to be encompassed by the present invention. In certain embodiments, the tubing is expanded radially by pressurizing the tubing from the inside out, introducing stress into the tube wall. This pressurizing can be conducted by any means capable of providing a differential pressure between the inside and outside of the tubing. Such differential pressure can be created by imposing a pressure above atmospheric pressure in the center of the tube, imposing a pressure below atmospheric pressure on the outside of the tube, or a combination of the two.

The stress induced into the wall of the tube causes it to expand outward. The rate of expansion can be controlled so the tube will hold the expanded state and not recover until subjected to a further heat cycle. The extent to which a tube is expanded depends on the application for which the tubing is intended. For example, in some embodiments, the tubing is expanded to an internal diameter of from about 1.05 times its original (unexpanded) diameter to about 10 times its original (unexpanded) diameter, such as from about 1.1 times its original (unexpanded) diameter to about 4 times its original (unexpanded) diameter.

In certain embodiments, the methods described for combining resins to form a multi-resin peelable heat shrink tubing as described above (i.e., the "blending" method and the "premix" method) may lead to tubing exhibiting different properties. For example, multi-resin tubing prepared according to the blending method may exhibit somewhat different properties along the length of the tubing. At any given point on such tubing, the tubing may exhibit properties that are more representative of one of the polymeric resin input materials. In contrast, multi-resin tubing prepared according to the premix method typically displays more uniform properties along the length of the tube, wherein the properties at any point along the tubing are substantially similar.

The single-resin and multi-resin tubings described herein can be produced in a wide range of sizes, including both variance in length, variance in diameter (i.e., expanded ID), and variance in wall thickness. For example, the length of tubings described herein can vary from individually-sized units (e.g., in some embodiments, on the order of 1-150 cm for catheter manufacturing) to lengths that can readily be transported and further cut into individually-sized units to large-scale production lengths (e.g., on the order of meters and the like). The diameters of tubings described herein can vary, in particular, depending upon the application for which the tubing is intended. Certain expanded IDs of the tubings described herein, particularly for medical uses, can range from about 0.01 cm to about 3 cm (e.g., between about 0.02 cm and about 2 cm or between about 0.025 cm and about 1.5 cm), although tubings having expanded IDs outside this range are also encompassed by the present invention, particularly in the context of applications in different fields. Tubing wall thicknesses can also vary. In certain exemplary embodiments, tubing wall thicknesses may vary from about 0.005 cm to about 0.5 cm, e.g., from about 0.01 cm to about 0.1 cm or from about 0.02 cm to about 0.05 cm. Again, these values relate to representative tubings, and tubings with wall thicknesses outside this range are also intended to be encompassed by the present invention.

The single-resin and multi-resin tubings provided according to the present invention can exhibit unique combinations of properties. As referenced above, certain tubings can exhibit heat shrink capability, longitudinal peelability, and translucency, as will be described in further detail below.

With regard to the heat shrink capabilities, in certain embodiments, the tubing is capable of shrinking (decreasing in diameter) when subjected to heat. Heat shrink materials are generally applied to an underlying material (e.g., a catheter construction, medical device component, etc.), and heated. When subjected to a further heat cycle, the inner diameter and the outer diameter of the tubing will decrease (resulting in a smaller inner diameter (ID) and a smaller outer diameter, OD, than that exhibited by the expanded tubing, referred to as the "recovered" ID and OD). Preferably, the tubing shrinks substantially only in diameter and not substantially in length (i.e., it shrinks in one plane only). The ratio between the expanded ID and the recovered ID is referred to as the expansion ratio. The expansion ratio is the expanded ID/recovered ID. Typical expansion ratios for the types of tubing described herein range from about 1.1:1 to about 6:1, such as from about 1.15:1 to about 2:1, and preferably from about 1.3:1 to about 1.65:1.

With regard to the longitudinal peelability, in certain embodiments, tubing provided according to the present disclosure is peelable lengthwise/longitudinally without use of any score lines, perforations, indentations, or the like. In certain such embodiments, a small nick, cut, or tear may be made at one end of the tubing to facilitate peeling of the tubing longitudinally (e.g., by hand). In other embodiments, no such nick, cut, or tear is required, and the tubing can be readily peeled (e.g., by hand) by pulling apart two sides of the tubing, beginning at one end of tubing. In certain embodiments, the tubing described herein may exhibit one or more of complete, straight, and even peeling along a given length of the tubing.

For example, in some embodiments, the tubing provided herein can exhibit one or more of complete, straight, and even peeling along at least about 1 meter of tubing, at least about 10 meters of tubing, or at least about 100 meters of tubing. In some embodiments, the tubing is cut into individual lengths, such as into individual tubes (e.g., with lengths tailored to particular applications). Of course, it is understood that sizes (both diameters and lengths) can be tailored for different applications and may be substantially larger or smaller than the examples noted herein. In certain embodiments, such tubes can be peeled completely and substantially evenly along their full lengths, as shown in FIG. 1, where the tubing is peeled, e.g., from end A to end B of the tubing to give two substantially equal longitudinal "halves" of tubing.

Figure 2:
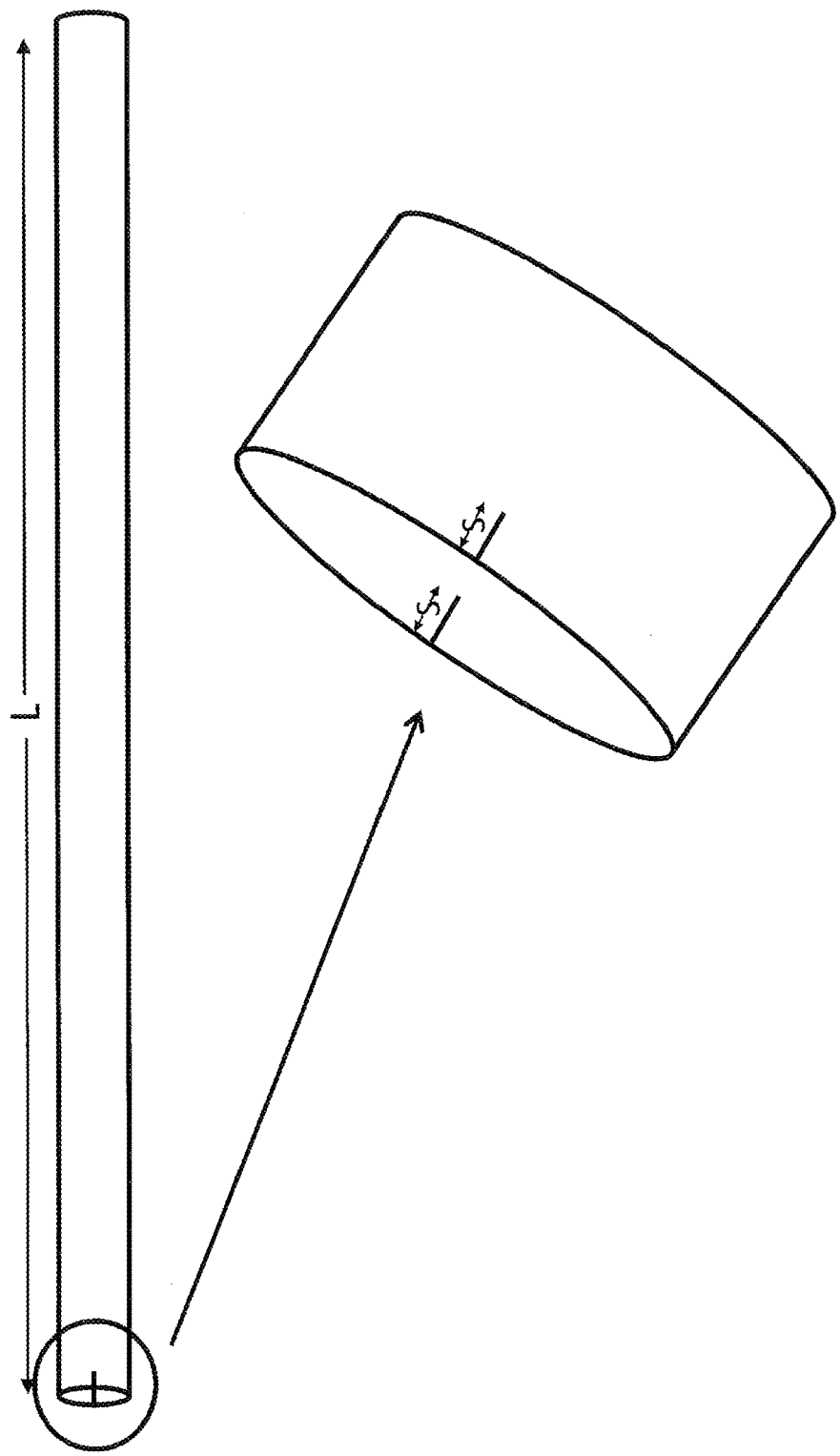
FIG. 2 is a schematic representation of a peelable tubing scored at one longitudinal end of the tubing.

In one particular embodiment, tubings provided according to the present disclosure can be scored, cut, or nicked across the cross-section of the tubing diameter at one end, as shown in FIG. 2 (providing a small score line or nick of length "S," e.g., about ½ inch or less in length). grasped (e.g., between the fingers or automated grips) and pulled/peeled without breaking or deviating from a substantially straight tear line for about 3 feet or more, or about 4 feet or more (including the entire length of the tubing, "L"). In some embodiments, the "peelability" or "tearability" can be achieved without any significant scoring or nicking. For example, in some embodiments, the score or nick across the cross-section of the tubing diameter has a length S that is less than about $1/10^{th}$ the length L of the tubing to be peeled, less than about $1/25^{th}$ the length L of the tubing to be peeled, less than about $1/50^{th}$ the length L of the tubing to be peeled, or less than about $1/75^{th}$ the length L of the tubing to be peeled. In some embodiments, such values can allow for complete peeling of the entire length of tubing and the peeled halves of tubing can be substantially equal in size (i.e., the tubing exhibits complete, straight, and/or even peeling along the entire length of the tubing).

The peel strength of the tubing materials described herein can vary. It is noted that preferred peel strengths vary with tubing diameter, with generally higher peel strengths preferred for larger diameters.

With regard to the translucency or transparency of certain tubings disclosed herein, in certain embodiments, the tubings exhibit translucency through one wall of the tubings. Translucency is understood to mean that light passes through the tubing wall but diffuses to some extent. In some embodiments, the tubings exhibit transparency through one wall of the tubing. Transparency is understood to mean that light passes through the tubing wall and does not diffuse to any significant extent.

The translucency and/or transparency of the tubing walls disclosed herein can be described by the total light % transmittance through the wall, the diffuse light % transmittance through the wall, and the haze %. Total light % transmittance compares the intensity of the light entering a sample with the intensity of the light leaving the sample. If a sample absorbs no light, the intensity of light entering the sample is equal to the intensity of the light leaving the sample, i.e., total light % transmittance is 100%. By contrast, if a sample absorbs the light completely, the intensity of light leaving the sample is 0, i.e., transmittance is 0%. Diffuse light % transmittance relates to the scattering of light entering the sample by comparing the intensity of light entering a sample at a given angle to the intensity of light leaving that sample at that same angle. Haze % is the ratio of diffuse % transmittance to total % transmittance. If a sample allows all light to pass through with the angle unchanged, the diffuse light % transmittance is 0%, the haze is 0%, and the sample is considered transparent. If, however, a sample diffuses any portion of the light entering the sample, the diffuse light transmittance is greater than 0%, the haze is above 0%, and the sample is not transparent (but may still be translucent). Relevant measurements can be made, for example, using a hazemeter or spectrophotometer, using methods known in the art (e.g., ASTM D1003-13, "Standard Test Method for Haze and Luminous Transmittance" (2015) and ASTM D1746-09, "Standard Test Method for Transparency of Plastic Sheeting" (2015), which are incorporated herein by reference).

The total light transmittance of certain tubings provided herein is advantageously at least about 80%, at least about 85%, or at least about 90%. The diffuse light transmittance is advantageously less than about 25%, less than about 20%, or less than about 15%. Based on these values, tubings described herein can, in some embodiments, be described as exhibiting low haze through the tubing wall, e.g., being substantially free of haze. In some embodiments, the tubings exhibit haze of less than about 50%, less than about 40%, less than about 30%, or less than about 20%. In some embodiments, the tubings can be described as being substantially (e.g., completely) free of haze, e.g., having a haze of less than about 15%, including less than about 12% and at least about 10%.

Consequently, the tubing may allow for users to readily see the underlying material when the heat shrink tubing is applied in use. For example, in some embodiments, the tubing exhibits light transmission through the tubing wall of at least about 80%, at least about 90%, at least about 95%, at least about 98%, or at least about 99% of available light. However, the tubing is not limited thereto and in certain embodiments, can be colored (e.g., via the incorporation of dyes or colorants) and/or somewhat less translucent and/or opaque.

Advantageously, the light transmittance values through the walls of the tubings disclosed herein are significant at all wavelengths within the visible range (i.e., about 400 nm to about 750 nm). For example, in certain embodiments, the total light % transmittance through the wall of a given tubing is at least about 25% across the full visible spectrum. In certain embodiments, the total light % transmittance through the wall of a given tubing is at least about 30%, at least about 35%, at least about 40%, at least about 45%, or at least about 50% across the full visible spectrum. All optical properties referenced herein relate to testing a single, flat tubing wall of substantially customary thickness for heat shrink tubes (e.g., having wall thicknesses as disclosed above).

In some multi-resin tubings, translucence and/or transparency of the tubing can be promoted by selecting appropriate resins for combination. For example, the optical clarity of a tubing produced from a combination of polymeric resins can be affected by the refractive indices of the constituent resins. Advantageously, to maximize the optical clarity of multi-resin tubings, constituent resins are selected having refractive indices that are similar (e.g., wherein all resins within a given multi-resin mixture have refractive indices within about 0.05 units or less, within about 0.04 units or less, within about 0.03 units or less, within about 0.02 units or less, or within about 0.01 units or less). Refractive indices of various resins are known and selection of resins to provide an optically clear tubing can be made based on these values. For example, a combination of FEP (with a refractive index of 1.34) and THV (with a refractive index of 1.35) would be expected to provide a clearer tubing than a combination of FEP (with a refractive index of 1.34) with PVDV (having a refractive index of 1.42).

Certain properties of the tubings disclosed herein can be evaluated by differential scanning calorimetry (DSC). DSC is an analytical technique that provides information on the thermal properties of materials, where the difference in a material's heat capacity is measured as a function of temperature. Generally, a material is subjected to a heat-cool-heat cycle to identify the thermal history. Subsequently, the material can be subjected to analysis to glean an understanding of polymer behavior post-uniform thermal history. When the material undergoes a physical transformation (e.g., a phase transition, such as melting), more or less heat is required to maintain the material at a constant temperature (depending on whether the phase transition is exothermic or endothermic) and this is shown as a peak (or valley) in the DSC trace. The heat capacity of the material at melting can be calculated using the integrated area under the melting peak in the DSC trace. DSC can be used, for example, to understand the relative crystallinity of materials, which can provide a better understanding of the translucency/transparency (optical clarity) and peelability, or potential for planned failure along a generally uniform axis or plane of the material.

In some embodiments, tubings exhibiting good optical properties (e.g., haze transmittance of greater than 15%) are provided, wherein the DSC traces indicate a dual melting peak and/or a broad melting peak. Such traces exhibited by tubings indicate that the composition of the tubings are polymorphic in nature. Dual melting peaks indicate that more than one distinct crystalline domain exists in the tubing material, as the only contributors to the melting process are crystalline domains.

DSC can also be used to understand the relative impact blending different polymers has on the crystallization kinetics and general molecular weight distribution of the material. In general, for semi-crystalline polymers, the longer the polymer chains, the higher the melting temperature and the narrower the melting range or melt peak observed by DSC analysis. The present invention relies, at least in part, on the onset of melting being significantly lower than that of the melting peak for the polymer of the resin of the single-resin tubings and significantly lower than that of the melting peak for any one or more of the polymers in the multi-resin tubings (e.g., the polymer having the lowest melting point of those present in the multi-resin tubing). In some embodiments, a broad melting range and an early onset of melting indicates the presence of low molecular weight material in the sample which, in some embodiments, can contribute to the desirable physical characteristics disclosed herein.

The breadth of the melting range can vary depending on the particular makeup of the tubing (i.e., the constituent resins or resins) and is indicative, e.g., of polymer blends with substantially different melting temperatures or polymer samples with a wide distribution of chain lengths. In general, a broad melting range may be indicative of suitable melt flow properties over a wide range of temperatures. In certain embodiments, the onset of melting (as shown by a deviation from the baseline in the DSC trace) is significantly lower than the melting point of the constituent polymer in a single-resin material (e.g., at least about 10 degrees less than the melting point of the polymer, at least about 20 degrees less than the melting point of the polymer, at least about 30 degrees less than the melting point of the polymer, at least about 40 degrees less than the melting point of the polymer, at least about 50 degrees less than the melting point of the polymer, at least about 60 degrees less than the melting point of the polymer). In certain embodiments, the onset of melting (as shown by a deviation from the baseline in the DSC trace) is significantly lower than the melting point of the primary resin in a multi-resin material (e.g., at least about 10 degrees less than the melting point of the polymer, at least about 20 degrees less than the melting point of the polymer, at least about 30 degrees less than the melting point of the polymer, at least about 40 degrees less than the melting point of the polymer, at least about 50 degrees less than the melting point of the polymer, at least about 60 degrees less than the melting point of the polymer). Advantageously, the onset of melting can, in some embodiments, be less than about 235° C. or less than about 230° C. Particularly, such an onset of melting is observed where data is collected at an increase of about 2° C. per minute (e.g., sweeping from 25° C. upwards, e.g., to 380° C.).

With respect to single-resin tubings, a broad melting range and/or two melting points can be achieved, e.g., by selection of a resin grade comprising lower melting species (e.g., oligomers). With respect to multi-resin tubings, the constituent resins can, in some embodiments, be selected such that a difference in the melting points of the resins provides a broad melting range in the final product (i.e., tubing). For example, a secondary resin can be selected so as to have a melting point significantly above or significantly below that of the main resin. The at least two melting points are advantageously at least partially merged in the DSC trace (i.e., to provide a broad melting range).

Accordingly, in certain embodiments, substantially translucent or transparent and peelable tubings disclosed herein exhibit a broad melting range and/or dual melting points. In particular embodiments, the melting range (i.e., the range of temperatures at which the DSC trace deviates from the baseline) is at least about 40° C., at least about 50° C., at least about 60° C., at least about 70° C., or at least about 80° C. and, advantageously, the tubing exhibits good optical clarity (e.g., haze transmittance of greater than 15%) and good peelability. One or more distinct "peaks" can be present within this range and typically at least one peak, corresponding to the melting point of the sole polymeric resin in a single-component tubing or the melting point of the primary polymeric resin in a multi-component tubing is observed.

Crystallinity can be further evaluated by x-ray diffraction. Percent crystallinity of a tubing material can be determined based on the relative intensities of amorphous and crystalline peaks in an x-ray diffraction pattern. In certain embodiments, lower crystallinity is desirable to provide a peelable material and/or a transparent or translucent material. For example, in some embodiments, the crystallinity of the tubing is less than about 40%, less than about 35%, or less than about 30%. Percent crystallinity can be determined based on the relative intensities of amorphous versus crystalline peaks of an x-ray diffraction pattern. Generally, such x-ray diffraction patterns exhibit a sharp peak representative of the crystalline material present in the sample (around 18 degrees, with other peaks appearing around 30 and 36 for FEP materials). Amorphous features are also generally observed in such x-ray diffraction patterns (one at the low angle of the primary crystalline peak and another around 40 degrees for FEP materials). The percent crystallinity can be calculated based on the following formula:

$$\% \text{ crystallinity} = [(I_c/(I_c+I_a)] \times 100\% \quad \text{(Formula 1)}$$

Wherein $I_c$ is the intensity of the crystalline peak(s) and $I_a$ is the intensity of the amorphous peak(s). The crystallinity of the material can, in some embodiments, affect the peelability and/or the translucence/transparency. For example, material with higher amorphous content has been observed to generally appear more transparent than material with lower amorphous content.

Accordingly, although not intended to be limiting, it is believed that the early onset of melting as exhibited by certain resins and resin blends and/or a somewhat low crystallinity exhibited by certain resins and resin blends can contribute to the unique properties observed for certain tubings disclosed herein. In particular, translucent and transparent tubings were surprisingly developed by using resins capable of providing tubing having particular melting properties and/or with particular crystallinity characteristics. It was unexpectedly found that tubings exhibiting certain crystallinity values (e.g., less than about 40% crystallinity as determined by x-ray diffraction) and/or certain early melting onset values (e.g., onset of less than about 230° C.) can provide the unique combination of properties of heat shrinkability, peelability, and translucence or transparency (as further detailed herein). Tubings described herein advantageously can, in certain embodiments, exhibit high transverse tensile strengths, but are not limited thereto.

In some embodiments, one or more additives can be incorporated within the tubing walls. For example, in certain embodiments, one or more additives can be included with the primary polymeric resin and secondary resin(s) and extruded with the mixture of resins (or with the single premix resin, in the case of the premix method). The additives can be in solid form (e.g., granular, powder, or pellet form) or can be in another form (e.g., gel form or liquid form, such as in the form of a dispersion or solution). In such embodiments, the one or more additives can be distributed (e.g., substantially uniformly) throughout the thickness and length of the tubing. In one particular embodiment, polytetrafluoroethylene (PTFE) is incorporated within the tubing described herein by adding PTFE powder to the resin(s) prior to extrusion. The type of PTFE powder that is incorporated in such embodiments can vary and may include conventional PTFE extrusion grade powder as well as PTFE granules, particles, and the like of various particle sizes. The incorporation of PTFE powder within a given type of tubing may, in some embodiments, increase the peelability of that tubing.

In exemplary embodiments described herein, the tubing is described as comprising a single composition; however, multi-composition tubing is also intended to be encompassed herein. For example, both single-layer and multi-layer constructions are provided according to the disclosure. A multilayer tubing can, in certain embodiments, be provided by co-extruding two or more types of material. Co-extruded tubing can comprise at least two layers, wherein one layer can be described as forming the inner diameter of the tubing and a second layer can be described as forming the outer diameter of the tubing. The number of layers can vary and a multilayered tubing is typically 2, 3, 4, or 5 total layers. In other embodiments, one or more additives can be introduced in one layer of a multilayer tubing construction. In such embodiments, at least one such layer comprises a peelable heat-shrink tubing composition as described throughout the present specification. In some embodiments, the co-extruded tubing can further comprise a second peelable heat-shrink tubing composition. In other embodiments, the co-extruded tubing can further comprise an alternative type of composition (i.e., a composition that is not necessarily a peelable heat-shrink tubing composition as described herein).

For example, in some embodiments, a co-extruded tubing is provided wherein the makeup of the two or more layers is substantially the same. For example, in some embodiments, the composition of one layer differs from the composition of a second layer only in the molecular weights of one component of the compositions thereof (e.g., the inner layer comprises 90% by weight FEP of molecular weight A and 10% by weight ETFE and the outer layer comprises 90% by weight FEP of molecular weight B and 10% by weight ETFE). In some embodiments, the composition of one layer differs from the composition of a second layer only in the ratio of polymeric resins used to produce the tubing (e.g., FEP:ETFE in a 80:20 ratio on the interior diameter and FEP:ETFE in an 85:15 ratio on the exterior diameter of the tubing). In some embodiments, the layers are substantially different (e.g., having different compositions). For example, in one embodiment, a two-layered tubing can be provided, wherein the inner layer comprises 90% by weight FEP and 10% by weight ETFE and the outer layer comprises 80% by weight FEP and 20% by weight PVDF.

In certain embodiments, the present disclosure provides a method for selecting a particular resin or resins (including at least one thermoplastic fluoropolymer) to produce a tubing exhibiting certain desirable properties. Advantageously, according to the present disclosure, one of skill in the art is provided with an understanding of the properties of component resins that can lead to the unexpected results outlined herein when such resin (or resins) are extruded into a tubing and subsequently converted into a heat shrinkable product.

For example, to provide a peelable heat shrink tubing exhibiting desirable optical properties (e.g., a tubing wherein the total light transmittance through the wall of tubing is about 90% or greater and wherein the diffuse light transmittance through the wall of the tubing is about 15% or less), the present disclosure outlines certain considerations. As detailed herein, for multi-resin tubings, one of skill in the art is guided to consider the refractive indices of the component resins as disclosed herein to ensure that they are within a limited range of each other (e.g., including but not limited to, within about 0.04). Further, one of skill in the art is guided to consider the crystallinity of the component resin or resins. He or she is aware of the melting points of various resin(s) and can select resins accordingly which exhibit a melting point onset that is below, and preferably significantly below (i.e., at a lower temperature than), the endothermic peak of the primary constituent resin in a resin blend or single-resin (e.g., including, but not limited to, below about 230° C.). Based on such understanding as provided in the present disclosure, one of skill in the art can intelligently select a resin or resins based on its physical characteristics to produce a tubing therefrom exhibiting the properties presented in detail herein.

It is noted that the properties disclosed herein are generally applicable to both the resins themselves and to the tubings produced therefrom. The disclosure refers to desirable characteristics of the tubings (including, but not limited to, desirable RI value differences in multi-resin tubings, desirable crystallinities, and/or desirable melt onset values) and it is understood that to select appropriate resins to provide such characteristics in the tubings, these characteristics in the resins are comparable. In other words, references to desirable tubing characteristics can be translated to the resins from which the tubings are produced. Accordingly, to develop a tubing exhibiting a given crystallinity or melt onset value to achieve the unique properties outlined herein, one of skill in the art, following the principles laid out in this disclosure, can base his or her property evaluation on the resin or resins to determine if, in resin form, the resin or resins exhibit such characteristics. As a specific example, to provide a tubing exhibiting a melting onset below 230° C., one can evaluate resins (prior to providing tubing therefrom) to determine whether any such resins exhibit a melting onset below 230° C. to provide the desired tubing.

Tubings provided herein can be used for a range of applications. In particular applications, they can be applied to an underlying material (e.g., devices, device components, joints, fittings, wires, etc.), and heated to form a covering thereon. Accordingly, the present disclosure encompasses materials or objects to which a tubing as disclosed herein has been applied. For example, in some embodiments, a covered device (e.g., medical device) comprising a tubing as disclosed herein is provided. Exemplary covered devices include, but are not limited to, medical devices (e.g., catheters) comprising any of the tubings disclosed herein applied thereto.

In one particular embodiment, a peelable, heat shrink tubing with optical clarity (e.g., high direct light transmittance) is provided for use as a component, processing aid or other aspect of a tube assembly. For example, such a tubing can be used where one or more sections of a tube assembly need to be re-flowed or fused, protected, covered, marked, or any use in which a traditional heat shrink may be used. Translucent and, particularly, transparent tubings as disclosed herein can provide advantages of direct, clear visualization of the area being covered and can allow for continued clear visualization after the heat shrink has been recovered. The ability to clearly visualize the underlying structures so alignment, proper placement and the potential for defect identification without removal of the heat shrink is critical in many fields. The presently disclosed tubings may be used as assembly aids or processing tools, such as where the material being covered with the heat shrink needs to be fused together. In such applications, the material being covered (e.g., at the end of the material) can be fused by applying the tubing to the material, identifying a temperature that is complementary to both the recovery or shrinking of the heat shrink tubing and the glassy or melt flow properties of the underlying material, and subjecting the assembly or materials to the elevated temperature to recover the heat shrink while softening the underlying material to a point of flow, whereby the material being covered may be thermally and/or mechanically bonded. The heat shrink tubing can then be removed from the assembly, as disclosed herein (e.g., in one or more generally uniform sections). The optical clarity and high direct light transmittance of certain tubings described herein allow this process to be carefully monitored for improvements and defect identification, as the underlying materials are visible through the tubing walls. The materials being fused together in such embodiments may be very soft and of low durometer, making them very sensitive to damage. Therefore, a material that does not tear or peel at all or is difficult to remove increases the risk of damaging the underlying materials and potentially creating failures or defects.

Accordingly, the present disclosure further relates to methods of using the tubings provided herein. Such methods generally comprise applying any of the tubings disclosed herein around at least a portion of a device comprising two or more components; heating the tubing to cause the tubing to shrink around the two or more components (and, in some embodiments, to cause at least one of the components to flow); cooling the shrunk tubing; and peeling the shrunk tubing from the device (with a degree of peelability as previously disclosed, e.g., to give two tubing halves of substantially equal size). The method can further comprise, for example, nicking or cutting the tubing across the cross-sectional diameter at an end of the tubing (e.g., along "S" as shown in FIG. 2), wherein the length S of the score line, cut, or nick is less than the length L of the tubing (including significantly less, as described in further detail above).

In addition, it is noted that although the present application focuses on the preparation of tubings, other products can be produced that exhibit the surprising and advantageous properties described herein. For example, a wide range of single-resin and multi-resin molded products can be formed in accordance with the disclosure and can, in some embodiments, exhibit the optical properties, peelability, and/or heat shrink properties disclosed herein.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A tubing, wherein the tubing is less than about 40% crystalline as determined by x-ray diffraction, and wherein the tubing exhibits heat shrink capability and longitudinal peelability.

2. The tubing of claim 1, wherein the tubing comprises one or more fluorinated resins.

3. The tubing of claim 1, wherein the tubing comprises one or more binary fluorinated copolymer resins.

4. The tubing of claim 1, wherein one or more fluorinated resins are selected from the group consisting of fluorinated ethylene propylene (FEP), polyvinylidene fluoride, perfluoroalkoxy alkane (PFA), perfluoro(alkyl vinyl ethers) (PAVE), a tetrafluoroethylene, hexafluoropropylene, and vinylidine fluoride terpolymer (THV), poly(ethylene-co-tetrafluoroethylene) (ETFE), ethylene chlorotrifluoroethylene (ECTFE), polychlorotrifluoroethylene (PCTFE), polytetrafluoroethylene (PTFE), tetrafluoroethylene and perfluoromethylvinyl ether copolymer (MFA), and copolymers, blends, and derivatives thereof.

5. The tubing of claim 1, wherein the tubing comprises no more than one resin.

6. The tubing of claim 1, wherein the tubing comprises two or more resins.

7. The tubing of claim 1, comprising no longitudinal physical score line, cut, or nick.

8. The tubing of claim 1, wherein the longitudinal peelability does not require a physical score line, cut, or nick or wherein the longitudinal peelability requires a physical score line, cut, or nick that is less than about $\frac{1}{50}^{th}$ the length of the tubing.

9. The tubing of claim 1, wherein the tubing exhibits a total light transmittance through a wall thereof of about 90% or greater.

10. The tubing of claim 1, wherein the tubing exhibits a total light transmittance through a wall thereof of about 95% or greater.

11. The tubing of claim 1, wherein the tubing exhibits a diffuse light transmittance of less than about 25%.

12. The tubing of claim 1, wherein the tubing exhibits a diffuse light transmittance of less than about 20%.

13. The tubing of claim 1, wherein the tubing exhibits a haze through a wall thereof of about 15% or less.

14. The tubing of claim 1, wherein the tubing exhibits a total light transmittance through a wall thereof of about 90% or greater and a diffuse light transmittance through the wall of about 25% or less.

15. The tubing of claim 1, wherein the tubing exhibits a melting point onset of less than about 230° C.

16. The tubing of claim 1, wherein the tubing exhibits two melting peaks when evaluated by differential scanning calorimetry.

17. The tubing of claim 1, wherein the tubing comprises no more than one resin, and wherein the tubing exhibits a melting point onset that is at least about 10 degrees lower than the melting point of the resin.

18. The tubing of claim 1, wherein the heat shrink capability, defined by expansion ratio of expanded ID to recovered ID is about 1.1:1 to about 6:1.

19. The tubing of claim 1, wherein the tubing is less than about 35% crystalline.

20. A medical device comprising the tubing of claim 1.

* * * * *